United States Patent
Matthews et al.

(10) Patent No.: US 10,012,634 B2
(45) Date of Patent: Jul. 3, 2018

(54) DISPLACEMENT MEASUREMENT CEMENT TESTING

(71) Applicant: Halliburton Energy Services, Inc., Houston, TX (US)

(72) Inventors: Kenneth Heidt Matthews, Kingwood, TX (US); James Robert Jones, Richmond, TX (US); Ketan Chimanlal Bhaidasna, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/029,168

(22) PCT Filed: Nov. 12, 2013

(86) PCT No.: PCT/US2013/069603
§ 371 (c)(1),
(2) Date: Apr. 13, 2016

(87) PCT Pub. No.: WO2015/072966
PCT Pub. Date: May 21, 2015

(65) Prior Publication Data
US 2016/0238586 A1  Aug. 18, 2016

(51) Int. Cl.
*E21B 47/005* (2012.01)
*G01B 21/32* (2006.01)
(Continued)

(52) U.S. Cl.
CPC ........... *G01N 33/383* (2013.01); *E21B 33/13* (2013.01); *E21B 47/0005* (2013.01); *G01B 21/32* (2013.01); *G01N 3/08* (2013.01)

(58) Field of Classification Search
CPC ....... E21B 33/13; E21B 47/0005; G01N 3/08; G01N 3/18; G01N 33/38; G01N 33/383; G01B 21/32
See application file for complete search history.

(56) References Cited

U.S. PATENT DOCUMENTS 8,443,661 B1  5/2013  Bi
2004/0221644 A1  11/2004  Boncan et al.
(Continued)

FOREIGN PATENT DOCUMENTS

WO  WO2013130227  9/2013

OTHER PUBLICATIONS

PCT International Search Report and Written Opinion of the International Searching Authority, PCT/US2013/069603, dated Aug. 8, 2014, 10 pages.

*Primary Examiner* — Nguyen Ha
(74) *Attorney, Agent, or Firm* — Tenley Krueger; Parker Justiss, P.C.

(57) ABSTRACT

A cement testing apparatus has a pressure vessel system defining a first interior volume sealed from a second interior volume. The pressure vessel system has a confining pressure port in fluid communication with the first interior volume and a rebalance pressure port in fluid communication with the second interior volume. A cement sample container is provided within the first interior volume. A displacement indicator is coupled to move with deformation of a cement sample supported by the sample container. The displacement indicator has a first portion inside the first interior volume, a second portion inside the second interior volume, and a third portion traversing a space between the first and second interior volumes.

19 Claims, 2 Drawing Sheets

(51) Int. Cl.
  *G01N 3/08*   (2006.01)
  *G01N 3/18*   (2006.01)
  *G01N 33/38*  (2006.01)
  *E21B 33/13*  (2006.01)
  *E21B 47/00*  (2012.01)

(56) References Cited

U.S. PATENT DOCUMENTS

| | | | |
|---|---|---|---|
| 2008/0178683 A1* | 7/2008 | Heathman | G01N 3/24 |
| | | | 73/803 |
| 2011/0061525 A1 | 3/2011 | Gray et al. | |
| 2011/0094295 A1 | 4/2011 | Meadows et al. | |
| 2013/0228019 A1* | 9/2013 | Meadows | G01N 3/08 |
| | | | 73/821 |
| 2013/0340505 A1* | 12/2013 | Go Boncan | G01N 33/383 |
| | | | 73/38 |

* cited by examiner

DISPLACEMENT MEASUREMENT CEMENT TESTING

CROSS-REFERENCE TO RELATED APPLICATIONS

This application is a U.S. National Phase Application under 35 U.S.C. § 371 and claims the benefit of priority to International Application Serial No. PCT/US2013/069603, filed on Nov. 12, 2013, the contents of which are hereby incorporated by reference.

TECHNICAL FIELD

This disclosure relates to determining mechanical properties of cement samples via displacement measurement cement testing.

BACKGROUND

Some well bores, for example some oil and gas wells, are lined with a casing. The cemented casing stabilizes the sides of the well bore, prevents fluids (liquids or gases) in the well bore from entering the surrounding earth formations, and/or prevents fluids from zones other than the producing zones from entering the well bore.

In a typical cementing operation, cement is introduced down the well bore and into an annular space between the casing and the surrounding earth. The cement secures the casing in the well bore, and prevents fluids from flowing vertically in the annulus between the casing and the surrounding earth.

Different cement formulations are designed for a variety of well bore conditions, which may be above or below ambient temperature and/or above ambient pressure. In designing a cement formulation, a number of potential cement slurry mixtures may be evaluated to determine their mechanical properties under various conditions.

BRIEF DESCRIPTION OF THE DRAWINGS

One or more features may be exaggerated or illustrated schematically to better show the features, process steps, and results. Like reference numbers and designations in the various drawings indicate like elements.

DETAILED DESCRIPTION

Using the apparatus and methods described in the present disclosure, mechanical properties of cement samples can be determined in simulated "downhole" conditions. In some examples, the cement samples can be cured at downhole conditions and then tested at desired intervals in the hydration process. In some examples, the curing or cured samples can be subjected to one or more tests (e.g., direct pull tensile strength tests and compressive strength tests) without removal of the samples from the pressure vessel being used to maintain simulated downhole conditions. One or more of the concepts described in the present disclosure are based on a realization that displacement measurements ascertained during testing may be influenced by the extreme downhole conditions maintained within the pressure vessel. Such displacement measurements can be improved in accuracy by compensating for the downhole conditions and/or by removing one or more of the cement testing apparatus' measurement components from the pressure vessel.

Figure 1:
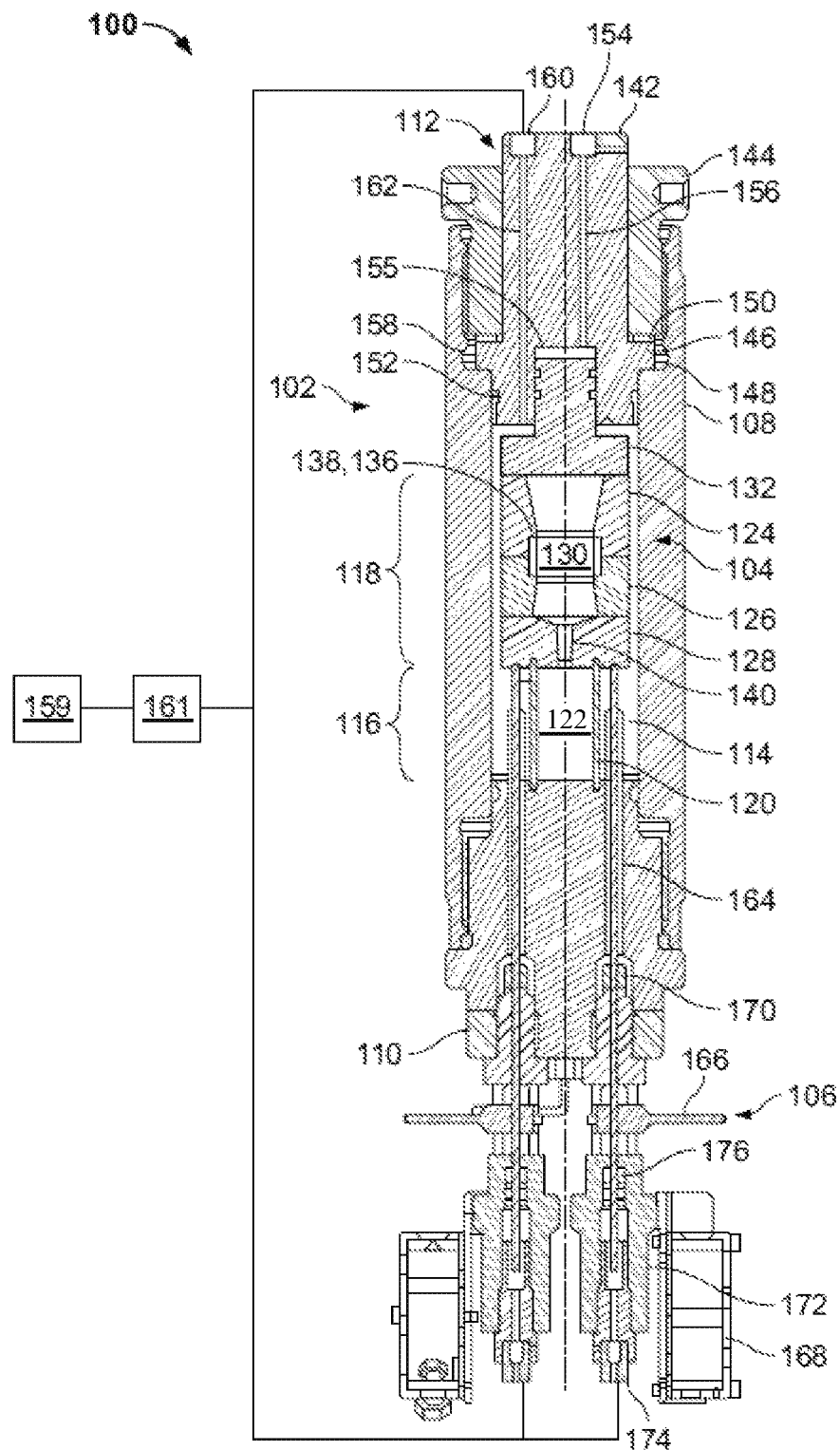
FIG. 1 is a half, cross-sectional view of a cement testing apparatus.

FIG. 1 is a half, cross-sectional view of an example cement testing apparatus 100. The testing apparatus 100 is specially designed to allow for sample testing under both compression and tension without changing components. However, it is appreciated that the concepts described in the present disclosure are not so limited, and can be incorporated in the design of various other types of cement testing apparatus.

As shown, the cement testing apparatus 100 includes a pressure vessel 102, a sample container 104, and a sensor package 106. The pressure vessel 102 includes a continuous side wall 108 extending between a lower end cap 110 and an upper end cap 112. The side wall 108, lower end cap 110, and upper end cap 112 cooperate to define a sealed interior volume 114. In this example, pressure vessel 102 is substantially cylindrical in shape. However, in some embodiments, the pressure vessel 102 can have other shapes (e.g., can be substantially rectangular in shape).

In this description, terms of relative orientation such as upper, lower, above, and below are used relative to the orientation of embodiments shown in the figures being discussed. Although such terms do not require that the illustrated apparatus components be oriented as shown in the figures, the cement testing apparatus 100 will typically be oriented as shown in FIG. 1 during use.

The sample container 104 is a sealed double-cell module, including a compression cell 116 and a tension cell 118. The sample container 104 is positioned near the axial centerline of the pressure vessel 102, such that an annular space of the pressure vessel's interior volume 114 surrounds the sample container. The compression cell 116 includes a first containment sleeve 120 press-fit at its lower end into a groove formed in an inner face of the pressure vessel's lower end cap 110. The first containment sleeve 120 extends upward from the lower end cap 110 to meet a lower wall member 128 of the tension cell 118. The first containment sleeve 120 is press-fit at its upper end into a groove formed in the base of the lower wall member 128. The first containment sleeve 120 provides the walls of the compression cell 116, defining a compression sample volume 122 sealed from the rest of the pressure vessel's interior volume 114.

The first containment sleeve 120 is designed to contain cement slurry as the slurry cures to form a cement sample, without providing significant resistance when compressive forces are applied to the cement sample. In this example, the first containment sleeve 120 is a rubber tube molded in a cylindrical shape having open ends. However, other configurations are also contemplated. For example, the first containment sleeve could be formed from a different material or a different shape, or formed using techniques other than molding (e.g., machining or laminating techniques from materials including, for example, epoxy, resins, and polymers).

The tension cell 118 is positioned directly above the compression cell 116 and directly below a piston 132. The tension cell 118 includes three wall members, an upper wall member 124, a middle wall member 126, and a lower wall member 128. The three wall members 124, 126, 128 cooperate to define a tension sample volume 130 in fluid communication with the compression sample volume 122, but sealed from the rest of the pressure vessel's interior volume 114. The tension sample volume 130 is axially aligned with the compression sample volume 122. Movement of the piston 132 in a downward direction applies compression to a portion of the cement sample in the compression sample volume 122, while movement of the piston upward applies tension to a portion of the cement sample in the tension sample volume 130. Each test can be performed in any order and with no influence over the adjacent portion of the cement sample.

The three wall members 124, 126, 128 and the piston 132 are connected in a specific manner to facilitate the independent tension and compression testing described above. In this example, the lower wall member 128 is mechanically attached to the middle wall member 126 to form a combined movable component 128,126. The movable component 128, 126 is mounted to the pressure vessel's lower end cap 110 (e.g., by extension rods, not shown). The mounting allows the movable component 128,126 to slide freely in the downward direction, but inhibits movement upward beyond the at-rest position shown in FIG. 1. The piston 132 is mechanically attached to the upper wall member 124. The upper wall member 124 abuts the middle wall member 126, but is not fixedly attached to the middle wall member. Thus the movable component 128,126 can be pressed downward by the piston 132 to bear on the portion of the cement sample in the compression sample volume 122, but does not move upward when the piston 132 pulls on the upper wall member 124.

The upper wall member 124 and the middle wall member 126 together define a recess 136 sized to receive a second containment sleeve 138. The second containment sleeve 138 is disposed extending across the interface between the middle wall member 126 and the upper wall member 124. Similar to the first containment sleeve 120, the second containment sleeve 138 is a rubber tube designed so as not to interfere with separate of the middle wall member 126 and the upper wall member 124 during tension testing.

The middle wall member 126 and the upper wall member 124 are tapered toward each other such that the tension sample volume 130 has a dog-bone shape with a narrow middle portion at the interface between the middle wall member 126 and the upper wall member 124 where the second containment sleeve 138 is seated. The portion of the cement sample in the tension sample volume 130 will typically fail in tension at this narrow middle portion when the upper wall member 124 is pulled away from the middle wall member 126.

The lower wall member 128 defines a channel 140 connecting the compression sample volume 122 and the tension sample volume 130. As described in more detail below, the compression sample volume 122 can be filled through the channel 140 in the lower wall member 128.

As described above, the pressure vessel 102 includes the side wall 108 extending between the lower end cap 110 and the upper end cap 112. In this example, the upper end cap 112 is a two-piece module, including an insert component 142 and a locking component 144 that secures the insert component to a top portion of the side wall 108. The insert component 142 defines an outwardly extending flange 146 that rests on the seat of a counter-bore 148. The locking component 144 is mechanically attached to the side wall 108, in this example by a set of mating threads, and bears down against the flange 146 of the insert component 142, pressing the flange tightly against the counter-bore 148. A gasket 150 seals the locking component 144 against the insert component 142. An O-ring 152 seals the insert component 142 against the side wall 108.

The insert component 142 includes a hydraulic port 154 connected to a channel 156 extending through the insert component and opening to a closed space 155 above the shaft of the piston 132. Hydraulic fluid (e.g., oil based fluid, water, etc.) used to control movement of the piston 132 is applied to the piston shaft through the hydraulic port 154 and the channel 156. O-rings 158 seal the space 155 from the rest of the interior volume 114 of the pressure vessel 102.

The insert component 142 also includes a confining pressure port 160 connected to a channel 162 extending through the insert component and opening to the interior volume 114. The confining pressure port 160 can be used, for example, to introduce pressurizing fluid into the annular space of the pressure vessel's interior volume 114 that surrounds the sample container 104. A fluid source 159 and a pump 161 supply pressurizing fluid to the confining pressure port 160. The temperature of the pressurized fluid can range from below ambient condition temperatures to the high temperatures associated with downhole conditions. Likewise, the pressure of the fluid can range from atmospheric pressure to the high pressures associated with downhole conditions. When high pressure fluid fills the pressure vessel's interior volume 114 it exerts a confining pressure on the cement sample in the sample container. The confining pressure provided by the pressurized fluid simulates an overburden pressure (i.e., the pressure from the weight of overlying rock, as well as other pressures, e.g. ambient hydrostatic pressures and/or other pressures) expected to be exerted on the cement lining of a well bore.

To accommodate the extreme conditions provided by the pressurized fluid introduced through confining pressure port 160, the components of the pressure vessel 102 can be made from materials which are strong (e.g., able to maintain structural stability when subjected to high pressures), are durable (e.g., resistant to corrosion by the anticipated pressurizing fluids in the anticipated temperature and pressure ranges), and can be formed with the precision necessary to maintain substantially pressure-tight engagement between the components under testing conditions. For example, the end caps 110, 112 and sidewall member 118 as well as the bottom, middle and top wall members can be machined from stainless steel. Alternatively, the end caps 110, 112 and sidewall member 108 can be formed using casting, laminating, or molding techniques from materials including, for example, steel, alloys, or composite fibers with a resin structure.

As noted above, the cement testing apparatus 100 includes a sensor package 106. The sensor package 106 is designed to characterize axial deformation of the portion of the cement sample in the compression sample volume 122 by measuring linear displacement of the lower wall member 128. The measurement of axial deformation can be used to determine various properties of the cement sample. For example, Young's Modulus, compressive strength, elastic limit, proportional limit, yield point, and yield strength. The following discussion describes a single sensor package. However, as shown, the cement testing apparatus 100 can have multiple sensor packages incorporated at various positions throughout the apparatus.

The sensor package 106 includes a displacement shaft 164, a displacement target 166, and a displacement sensor 168. The top end of the displacement shaft 164 is mechanically connected to the lower wall member 128, such that movement of the lower wall member, when the piston 132 is moved downward during compression testing, causes identical movement of the displacement shaft. The displacement shaft 164 extends downward from the lower wall member 128, through the pressure vessel's interior volume 114, and through the lower end cap 110 to protrude outward beyond the pressure vessel 102. A dynamic seal 170 seals the pressure vessel's interior volume 114. The bottom end of the displacement shaft 164 is received by a pressure rebalance housing 172. A dynamic seal 176 seals the pressure rebalance housing 172. The pressure rebalance housing 172 includes a rebalance pressure port 174, allowing pressurized fluid from the fluid source 159 and pump 161 to enter the pressure rebalance housing.

The displacement target 166 is fixedly coupled to the displacement shaft 164 outside the pressure vessel 102, such that movement of the displacement shaft causes identical movement of displacement target relative to the displacement sensor 168. The displacement sensor 168 is positioned below the displacement target 166. In this example, the displacement sensor 168 is a laser displacement sensor producing a field of detection aimed at the displacement target 166. However any type of sensor suitable for measuring micro scale displacement could be used. For example, linear variable displacement transducer sensors (LVDTs), magnetic drive sensors, acoustic sensors, etc. can be used without departing from the scope of the present disclosure.

In this configuration, the displacement sensor 168 of the sensor package 106 is positioned outside the pressure vessel 102, and is therefore shielded from the extreme conditions caused by the pressurized fluid used to introduce the cement sample to downhole conditions. This configuration is advantageous because the displacement sensor 168 does not need to be engineered to withstand the anticipated downhole conditions, and because the resiliency of the displacement sensor is not a constraint on the range of temperature and pressure introduced to the pressure vessel's internal volume 114. Additionally, because the displacement sensor 168 has been moved away from the pressure vessel 102, problems with interference from the pressure vessel on the measurement signal of the displacement sensor are diminished. This effect is especially advantageous when magnetic sensors (e.g., LVDTS or magnetic drive sensors) are used, because the components of the pressure vessel are not limited to non-magnetic materials.

Figure 2:
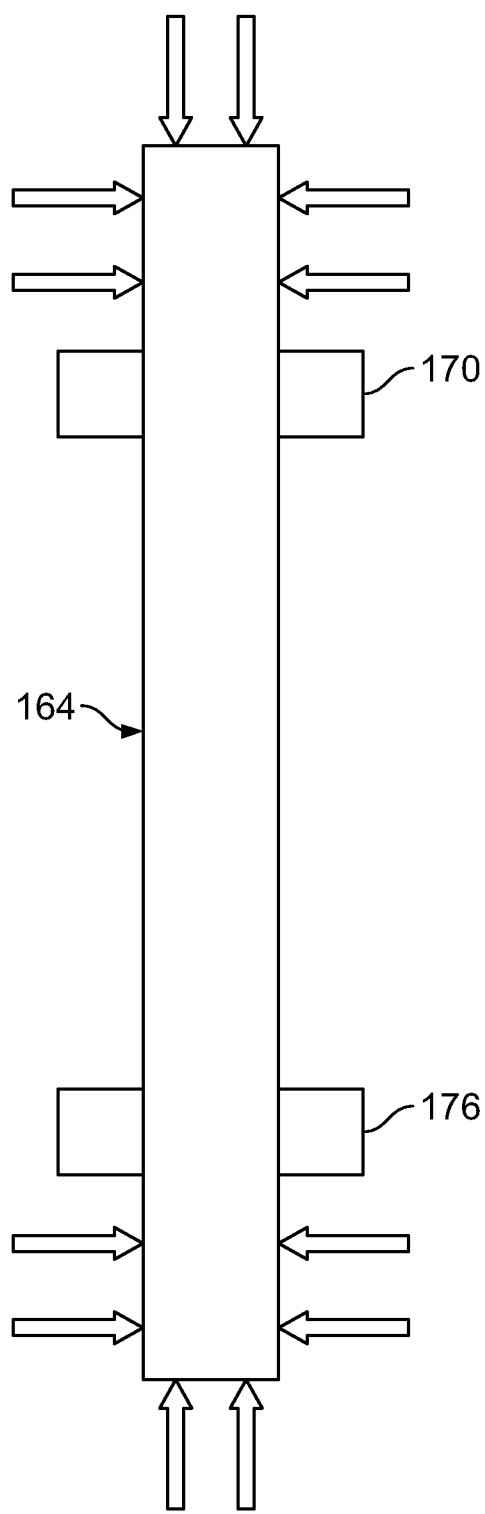
FIG. 2 is a diagram illustrating pressure forces exerted on a displacement shaft of the cement testing apparatus of FIG. 1.

FIG. 2 is a diagram illustrating pressure forces exerted on the displacement shaft 164 of the cement testing apparatus 100. In this example, the pressurized fluid in the pressure vessel's internal volume 114 exerts a confining pressure on the top end of the displacement shaft 164. As noted above, the pressure rebalance housing 172 also receives pressurized fluid from the fluid source 159 and pump 161 via the rebalance pressure port 174. Thus a rebalance pressure opposing the confining pressure is exerted on the bottom end of the displacement shaft 164. The rebalance pressure is equal in magnitude to the confining pressure. In this configuration, the displacement shaft is held in balance between the pressure vessel 102 and the pressure rebalance housing 172. That is, the pressure rebalance housing 172 inhibits (or entirely prevents) any measurement bias that could be introduced by the extreme confining pressure in the pressure vessel's internal volume 114.

A user preparing and filling the cement testing apparatus 100 for testing of a cement sample begins by attaching the first containment sleeve 120 to the lower end cap 110 and to the tension cell's lower wall member 128. The tension cell's middle wall member 126 is placed on top of the lower wall member 128 and mechanically attached to the lower wall member (e.g., using screws) to form the movable component 128,126. The movable component 128,126 is mounted to the pressure vessel's lower end cap 110. The top end of the displacement shaft is eased through the lower end cap 110 and attached to the lower wall member 128. The bottom end of the displacement shaft 164 is installed in the pressure rebalance housing 172, with the displacement target being positioned between the pressure vessel 102 and the pressure rebalance housing. The second containment sleeve 138 is then inserted into the portion of recess 136 defined by the middle wall member 126. The upper wall member 124 is then placed on top of the middle wall member 126. The side wall 108 of the pressure vessel 102 is then lowered around the compression cell 116 and the tension cell 118 and attached to the lower end cap 110.

A cement slurry composition to be tested is dispensed into the testing apparatus 100 through the open upper end of the upper wall member 124 to fill the compression sample volume 122 and the tension sample volume 130. The piston 132 is placed atop the upper wall member 124 and mechanically attached thereto (e.g., using screws). The insert component 142 of the pressure vessel's upper end cap 112 is placed in the counter-bore 148 provided by the side wall 108. The locking component 144 is then installed to secure the insert component 142 in place against the side wall's counter-bore 148.

The cement slurry can be cured or partially cured at controlled temperatures and pressures to simulate, for example, downhole conditions before testing. A temperature stable pressurizing fluid such as, for example, water is pumped from fluid source 159 by pump 161 into the annular space of pressure vessel's interior volume 114, between the components of the sample container 104 and the side wall 108. The confining pressure applied to sides of the cement sample can be controlled using the pressurizing fluid. In some examples, the cement slurry is allowed to cure for a specified time with an equal pressure applied to the top of the piston 132 and into the annular space of the interior volume 114. Temperature can be controlled to simulate downhole conditions during testing or at other times. For example, in testing cement, the testing apparatus 100 and cement slurry can be preheated during mixing. The desired temperature can be maintained as the sample cement composition cures using external heating elements (e.g., heater coils or stainless steel heater bands) or placing the testing apparatus 100 in an oven; cooling coils can also be employed if temperatures below ambient conditions are desired. Likewise the testing apparatus could also be heated in a profile that simulates the temperature a cement system would experience from mixing, placement, and curing during cementing a wellbore casing string. After the cement slurry has cured the desired degree, compression and tension testing are performed by regulating the pressure applied to the piston 132.

Compression testing is performed by increasing the hydraulic pressure applied to the piston 132. Increasing the pressure applied to the piston 132 biases the piston towards the cement sample and biases the entire tension cell 118 to towards the compression cell 116. The hydraulic pressure is applied to the piston 132 is increased until the portion of the cement sample in the compression sample volume 122 fails in compression Tension testing is performed by decreasing the hydraulic pressure applied to the piston 132. As described above, the piston 132 is attached to the upper wall member 124, but the upper wall member is not attached to the middle wall member 126. Thus decreasing the pressure applied to the piston 132, which biases the piston away from the cement sample, pulls the upper wall member 124 away from the middle wall member 126 and the lower wall member 128. The pressure applied to the piston 132 is decreased until, in some cases, the portion of the cement sample in the tension sample volume 130 fails in tension; in other cases, stresses are applied up to certain levels of the ultimate stress of the sample for instance to study the sample reaction to cyclic loading events. Both the compression and tension testing can be performed in any order without affecting the integrity of the adjacent portion of the sample.

A particular of example cement testing apparatus has been described in detail. Nevertheless, it will be understood that various modifications may be made without departing from the spirit and scope of the present disclosure. For example, a sensor package 106 could be adapted to take displacement measurements during tension testing of the cement sample in addition to (or in place of) of the measurements described above during compression testing. Further, while the above-described example sensor package 106 characterizes axial deformation, other types of sensor packages are also envisioned. For example, sensor packages that characterize lateral deformation (e.g., by measuring displacement of a laterally oriented shaft) to determine Poison's Ratio or sensor packages that characterize deformation under torsional loads (e.g., by measuring rotational displacement of a shaft arranged to rotate with torsional deformation of the sample) to determine shear properties of the cement sample. Further still, while the pressure rebalance housing 172 and the pressure vessel 102 are shown and described as separate structures, it is contemplated that these components could be incorporated in a single, monolithic housing with the pressure vessel's internal volume 114 being sealed from the internal volume of the rebalance housing.

What is claimed is:

1. A cement testing apparatus, comprising:
   a pressure vessel system defining a first interior volume sealed from a second interior volume, the pressure vessel system comprising a confining pressure port in fluid communication with the first interior volume and a rebalance pressure port in fluid communication with the second interior volume;
   a cement sample container within the first interior volume; and
   a displacement indicator coupled to move with deformation of a cement sample supported by the sample container, the displacement indicator having a first portion inside the first interior volume, a second portion inside the second interior volume, and a third portion traversing a space between the first and second interior volumes.

2. The cement testing apparatus of claim 1, where the pressure vessel system comprises a testing pressure vessel defining the first interior volume and a rebalance pressure vessel defining the second interior volume.

3. The cement testing apparatus of claim 1, where the confining pressure port and the rebalance pressure port are coupled to receive the same pressure from a pressure source.

4. The cement testing apparatus of claim 1, where the rebalance pressure port is positioned to exert a pressure force on the displacement indicator that opposes a pressure force exerted on the displacement indicator via the confining pressure port.

5. The cement testing apparatus of claim 1, comprising a piston assembly coupled to the sample container and configured to apply stress to the cement sample.

6. The cement testing apparatus of claim 5, where the displacement indicator is coupled to the piston assembly, with movement of the piston assembly effecting movement of the displacement indicator.

7. The cement testing apparatus of claim 1, where the displacement indicator comprises an elongated rod movable linearly in a direction parallel to an axis of the sample container.

8. The cement testing apparatus of claim 1, where the first portion of the displacement indicator is sealed from the second portion of the displacement indicator.

9. The cement testing apparatus of claim 1, where the sample container comprises a compression cell and a tensile cell, each of which is configured to receive a cement sample.

10. The cement testing apparatus of claim 1, comprising a displacement sensor positioned outside the pressure vessel and configured to detect movement of the displacement indicator.

11. A cement tester, comprising:
    a pressure vessel system defining a first interior volume sealed from a second interior volume;
    a cement sample container within the first interior volume;
    a displacement indicator coupled to move with deformation of a cement sample supported by the sample container, the displacement indicator having a first portion inside the first interior volume and a second portion at least partially within the second interior volume;
    a displacement target coupled to the displacement indicator; and
    a displacement sensor supported outside the pressure vessel system and configured to detect movement of the displacement target.

12. The cement tester of claim 11, comprising a pressure source applying equal pressure to the first mentioned interior volume and the second interior volume.

13. The cement tester of claim 11, where the displacement indicator comprises a rod coupled to a piston in the first interior volume.

14. A method of testing a cement sample, the method comprising:
    controlling a confining pressure within a first interior volume of a cement testing apparatus, the confining pressure bearing on a first portion of a displacement indicator coupled to move with deformation of a cement sample held by a cement sample container within the first interior volume; and
    controlling a rebalance pressure within a second interior volume to substantially match the confining pressure, the second interior volume being sealed from the first interior volume, and the rebalance pressure bearing on a second portion of the displacement indicator, with a third portion of the displacement indicator traversing a space between the first and second interior volumes.

15. The method of claim 14, comprising controlling a temperature within the first interior volume.

16. The method of claim 14, comprising:
    applying stress to the cement sample; and
    measuring deformation of the cement sample in the space between the first and second interior volumes.

17. The method of claim 14, where measuring deformation of the cement sample comprises tracking movement of a displacement target coupled to the third portion of the displacement indicator.

18. The method of claim 14, where applying stress to the cement sample comprises moving a piston assembly coupled to the sample container.

19. The method of claim 14, where the sample container comprises a compression cell and a tensile cell; and comprising:

applying compressive stress to a portion of the cement sample in the compression cell;
applying tensile stress to a portion of the cement sample in the tensile cell; and
measuring deformation of the cement sample in the space between the first and second interior volumes.

* * * * *